United States Patent
Newton et al.

(10) Patent No.: US 6,376,393 B1
(45) Date of Patent: Apr. 23, 2002

(54) METHOD FOR PRODUCING ANISOTROPIC DIELECTRIC LAYER AND DEVICES INCLUDING SAME

(75) Inventors: Mike Newton, Palm Bay, FL (US); Joseph P. Dougherty, State College, PA (US); Else Breval, State College, PA (US); Maria Klimkiewicz, State College, PA (US); Yi Ton Shi, State College, PA (US); Dean Arakaki, State College, PA (US)

(73) Assignee: Harris Corporation, Melbourne, FL (US)

( * ) Notice: Subject to any disclaimer, the term of this patent is extended or adjusted under 35 U.S.C. 154(b) by 0 days.

(21) Appl. No.: 09/224,044

(22) Filed: Dec. 31, 1998

Related U.S. Application Data (63) Continuation-in-part of application No. 08/858,005, filed on May 16, 1997.

(51) Int. Cl.$^7$ ................................................. H01L 21/31
(52) U.S. Cl. ........................................ 438/783; 438/784
(58) Field of Search ................................. 438/783, 610, 438/784, 780, 782

(56) References Cited

U.S. PATENT DOCUMENTS

| | | | |
|---|---|---|---|
| 4,548,862 A | * | 10/1985 | Hartman |
| 4,838,347 A | * | 6/1989 | Dentini et al. |
| 4,911,981 A | * | 3/1990 | Schnur et al. |
| 5,096,551 A | * | 3/1992 | Schoen, Jr. et al. |
| 5,769,996 A | * | 6/1998 | McArdle et al. ......... 156/272.4 |

* cited by examiner

Primary Examiner—Caridad Everhart
(74) Attorney, Agent, or Firm—Allen, Dyer, Doppelt, Milbrath & Gilchrist, P.A.

(57) ABSTRACT

A method for making an anisotropic dielectric layer includes the steps of: forming a fluid layer comprising a plurality of magnetizable particles, for example, in a fluid capable of solidifying to fix the configuration of the magnetizable particles in a dielectric matrix; aligning the magnetizable particles of the fluid layer in a predetermined configuration by applying a magnetic field thereto; and fixing the aligned magnetizable particles in the predetermined configuration within the dielectric matrix by solidifying the fluid. In one particularly advantageous application, the fluid layer is coated onto a surface portion of an integrated circuit, such as a fingerprint sensor, to provide mechanical protection without effecting the image resolution. In addition, the step of aligning for certain devices preferably comprises aligning the magnetizable particles in a predetermined configuration so that an impedance perpendicular to the anisotropic dielectric layer is less than an impedance parallel to the anisotropic dielectric layer. The magnetizable particles may be mixed in a curable polymer fluid, and the step of fixing the aligned magnetizable particles may comprise curing the curable polymer fluid, such as by applying heat or radiation.

9 Claims, 7 Drawing Sheets

METHOD FOR PRODUCING ANISOTROPIC DIELECTRIC LAYER AND DEVICES INCLUDING SAME

RELATED APPLICATION

The present application is a continuation-in-part patent application of U.S. patent application Ser. No. 08/858,005 filed May 16, 1997, and the entire disclosure of which is incorporated herein in its entirety by reference.

FIELD OF THE INVENTION

The present invention relates to the field of materials, and, more particularly, to the field of semiconductor materials having certain dielectric properties.

BACKGROUND OF THE INVENTION

Semiconductor devices are widely used in many applications. For example, an early version of an integrated circuit fingerprint sensor produced by Harris Corporation was based upon sensing an electric field between the sensor and the ridges and valleys of a fingerprint of a user. Such a sensor may be extremely accurate in generating an image of the ridges and valleys of the fingerprint.

The fingerprint sensor relied on direct contact between the finger of the user and the integrated circuit. Such direct contact can lead to several difficulties with regards to the long term reliability of the sensor. For example, sodium ions from perspiration may migrate through the relatively thin outer passivation layer or layers and adversely affect the semiconductor material of the sensor. Solvents for cleaning the sensing surface may also damage the integrated circuit.

Typical passivation layers for integrated circuit technologies are relatively thin, since the IC is usually protected by an overall body of molded encapsulating material. The encapsulating material provides both mechanical protection, as well as protection from contamination of the semiconductor material. Unfortunately, in an application such as the electric field fingerprint sensor, the IC die itself must be exposed to direct contact. Moreover, simply increasing the thickness of passivation or protective coatings may reduce the quality of the fingerprint image. This is so because the electric fields of the individual pixel elements of the sensor tend to curve or defocus as the spacing between the elements and the finger is increased.

U.S. Pat. No. 4,353,056 to Tsikos discloses an early approach to sensing a live fingerprint. In particular, the patent discloses an array of extremely small capacitors located in a plane parallel to the sensing surface of the device. When a finger touches the sensing surface and deforms the surface, a voltage distribution in a series connection of the capacitors may change. Unfortunately, the resilient materials required for the sensor may suffer from long term reliability problems. Moreover, noise and stray capacitances may adversely affect the plurality of relatively small and closely spaced capacitors.

U.S. Pat. No. 5,325,442 to Knapp discloses another fingerprint sensor and which includes a plurality of sensing electrodes. A capacitor is effectively formed by each sensing electrode in combination with the respective overlying portion of the finger surface which, in turn, is at ground potential. The sensor may be fabricated using semiconductor wafer and integrated circuit technology. The dielectric material upon which the finger is placed may be provided by silicon nitride or a polyimide which may be provided as a continuous layer over an array of sensing electrodes.

Unfortunately, such conventional semiconductor related materials and their relative thinness may not be sufficient for direct contact by the finger of a user. Moreover, increasing the thickness of any coating layer may adversely affect the image accuracy or resolution. Accordingly, at present the designer needs to sacrifice robustness of the IC fingerprint sensor to obtain sufficient accuracy in the image produced.

SUMMARY OF THE INVENTION

In view of the foregoing background, it is therefore an object of the present invention to provide a method for making a dielectric layer, such as for integrated circuits, that is relatively thick, yet which has reduced defocusing of an electric field passing therethrough.

It is another object of the present invention to provide integrated circuits and layers having a dielectric layer with certain desirable dielectric properties.

These and other objects, features, and advantages in accordance with the present invention are provided by a method for making an anisotropic dielectric layer comprising the steps of: forming a fluid layer comprising a plurality of magnetizable particles in a fluid capable of solidifying to fix the configuration of the magnetizable particles in a dielectric matrix; aligning the magnetizable particles of the fluid layer in a predetermined configuration by applying a magnetic field thereto; and fixing the aligned magnetizable particles in the predetermined configuration within the dielectric matrix by solidifying the fluid to thereby make the anisotropic dielectric layer. In one particularly advantageous application, the fluid layer is coated onto a surface portion of an integrated circuit, such as a fingerprint sensor, to provide mechanical protection without effecting the image quality or resolution. In addition, the step of aligning for certain devices preferably comprises aligning the magnetizable particles in a predetermined configuration so that an impedance in a direction perpendicular to the anisotropic dielectric layer is less than an impedance in a direction parallel to the anisotropic dielectric layer.

The magnetizable particles may be mixed in a curable polymer fluid, and the step of fixing the aligned magnetizable particles may comprise curing the curable polymer fluid, such as by applying heat or radiation. The magnetizable particles may be generally spherical having diameters in a range of about 1 to 3 microns. The magnetizable particles may also be generally elongate.

The method may also include the step of controlling a viscosity of the fluid by incorporating dielectric particles in the fluid. For example, the size and/or concentration of the dielectric particles may be controlled in the curable polymer fluid. The dielectric particles may also reduce lateral coupling of the magnetizable particles.

The step of aligning the magnetizable particles preferably comprises applying a substantially uniform magnetic field to the fluid layer, such as achieved by positioning a pair of opposing magnets adjacent opposite sides of the fluid layer and extending laterally outwardly beyond edges thereof.

An integrated circuit including the anisotropic layer preferably also comprises a substrate, and a semiconductor layer adjacent the substrate. The anisotropic dielectric layer is preferably adjacent the semiconductor layer, and the anisotropic dielectric layer preferably comprises a dielectric matrix and a plurality of aligned magnetizable particles therein. The magnetizable particles may be aligned in a predetermined direction so that the anisotropic dielectric layer has an impedance in a direction perpendicular to a surface being less than an impedance in a parallel direction.

In addition, the semiconductor layer may include means for passing an electric field through the anisotropic dielectric layer, such as for sensing applications.

Another aspect of the invention relates to the dielectric layer. The dielectric layer preferably comprises a plurality of aligned magnetizable particles fixed in a dielectric matrix, such as to provide an impedance in a first direction which is less than an impedance in a second direction transverse to the first direction.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout and prime notation is used to indicate similar elements in alternate embodiments. The scaling of various features, particularly layers in the drawing figures, have been exaggerated for clarity of explanation.

Figures 1, 2:
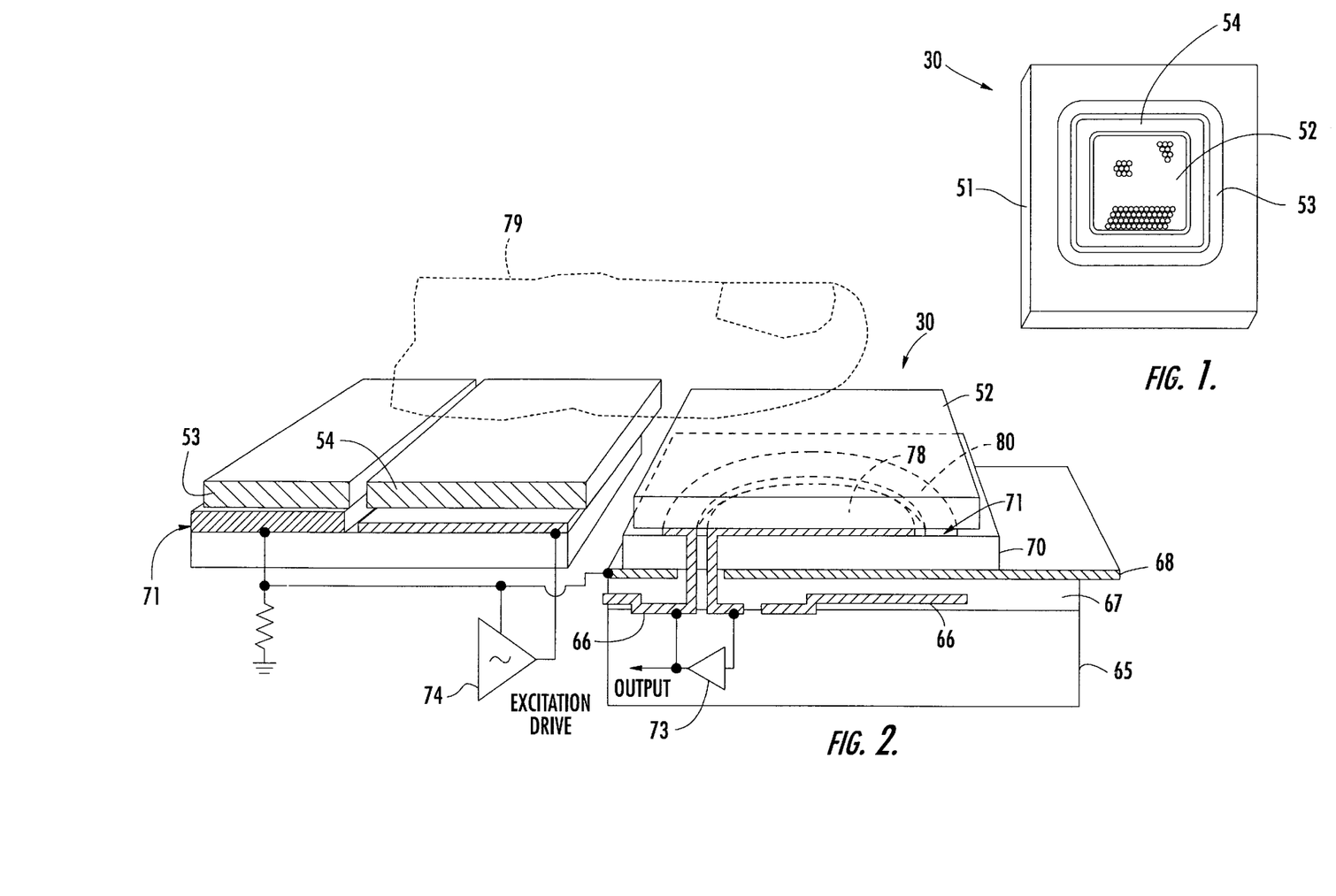
FIG. 1 is a plan view of a fingerprint sensor including the anisotropic dielectric layer as an outer surface layer in accordance with the present invention.
FIG. 2 is an enlarged schematic cross-sectional view of a portion of the fingerprint sensor including an anisotropic dielectric layer as shown in FIG. 1.
Figure 3:
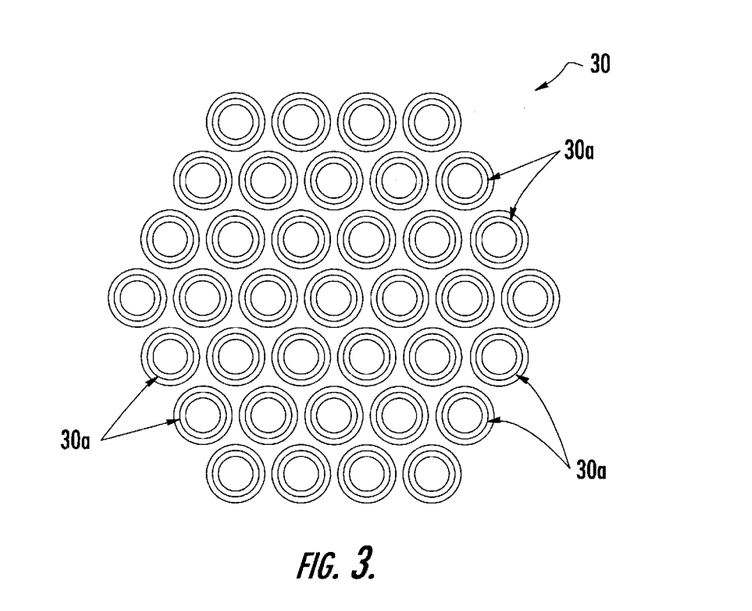
FIG. 3 is a greatly enlarged view of a plurality of electric field sensing elements or pixels used in the fingerprint sensor shown in FIG. 1.

Referring to FIGS. 1–3, a fingerprint sensor 30 including the anisotropic dielectric layer 52 in accordance with the invention is initially described. The illustrated sensor 30 includes a housing or package 51, the anisotropic dielectric layer 52 exposed on an upper surface of the package which provides a placement surface for the finger, and a plurality of output pins, not shown. A first conductive strip or external electrode 54 around the periphery of the dielectric layer 52, and a second external electrode 53 provide contact electrodes for the finger 79 as described in greater detail below. The sensor 30 may provide output signals in a range of sophistication levels depending on the level of processing incorporated in the package as would be readily understood by those skilled in the art.

The sensor 30 includes a plurality of individual pixels or sensing elements 30a arranged in array pattern as perhaps best shown in FIG. 3. As would be readily understood by those skilled in the art, these sensing elements are relatively small so as to be capable of sensing the ridges 59 and intervening valleys 60 of a typical fingerprint. As will also be readily appreciated by those skilled in the art, live fingerprint readings as from the electric field sensor 30 in accordance with the present invention may be more reliable than optical sensing, because the impedance of the skin of a finger in a pattern of ridges and valleys is extremely difficult to simulate. In contrast, an optical sensor may be deceived by a photograph or other similar image of a fingerprint, for example.

The sensor 30 includes a substrate 65, and one or more active semiconductor devices formed thereon, such as the schematically illustrated amplifier 73. A first metal layer 66 interconnects the active semiconductor devices. A second or ground plane electrode layer 68 is above the first metal layer 66 and separated therefrom by an insulating layer 67. A third metal layer 71 is positioned over another dielectric layer 70. In the illustrated embodiment, the first external electrode 54 is connected to an excitation drive amplifier 74 which, in turn, drives the finger 79 with a signal that may be typically in the range of about 1 KHz to 1 MHZ. Accordingly, the drive or excitation electronics are thus relatively uncomplicated and the overall cost of the sensor 30 may be relatively low, while the reliability is great.

An illustratively circularly shaped electric field sensing electrode 78 is on the insulating layer 70. The sensing electrode 78 may be connected to sensing integrated electronics, such as the illustrated amplifier 73 formed adjacent the substrate 65 as schematically illustrated, and as would be readily appreciated by those skilled in the art.

An annularly shaped shield electrode 80 surrounds the sensing electrode 78 in spaced relation therefrom. As would be readily appreciated by those skilled in the art, the sensing electrode 78 and its surrounding shield electrode 80 may have other shapes, such as hexagonal, for example, to facilitate a close packed arrangement or array of pixels or sensing elements 30a. The shield electrode 80 is an active shield which is driven by a portion of the output of the amplifier 73 to help focus the electric field energy and, moreover, to thereby reduce the need to drive adjacent electric field sensing electrodes 78.

The sensor 30 illustratively includes only three metal or electrically conductive layers 66, 68 and 71. The sensor 30 can be made without requiring additional metal layers which would otherwise increase the manufacturing cost, and, perhaps, reduce yields. Accordingly, the sensor 30 is less expensive and may be more rugged and reliable than a sensor including four or more metal layers as would be appreciated by those skilled in the art.

Another aspect of the present invention is that the amplifier 73 may be operated at a gain of greater than about one to drive the shield electrode 80. Stability problems do not adversely affect the operation of the amplifier 73. Moreover, the common mode and general noise rejection are greatly enhanced. In addition, the gain greater than one tends to focus the electric field with respect to the sensing electrode 78 as will be readily appreciated by those skilled in the art.

In general, the sensing elements 30a operate at very low currents and at very high impedances. For example, the output signal from each sensing electrode 78 is desirably about 5 to 10 millivolts to reduce the effects of noise and permit further processing of the signals. The approximate diameter of each sensing element 30a, as defined by the outer dimensions of the shield electrode 80, may be about 0.002 to 0.005 inches in diameter. The ground plane electrode 68 protects the active electronic devices from unwanted excitation. The various signal feedthrough conductors for the electrodes 78, 80 to the active electronic circuitry may be readily formed as would be understood by those skilled in the art.

The overall contact or sensing surface for the sensor 30 may desirably be about 0.5 by 0.5 inches—a size which may be readily manufactured and still provide a sufficiently large surface for accurate fingerprint sensing and identification. The sensor 30 in accordance with the invention is also fairly tolerant of dead pixels or sensing elements 30a. A typical sensor 30 includes an array of about 256 by 256 pixels or sensor elements, although other array sizes are also contemplated by the present invention. The sensor 30 may also be fabricated at one time using primarily conventional semiconductor manufacturing techniques to thereby significantly reduce the manufacturing costs.

Turning additionally to FIGS. 4–8, the anisotropic dielectric layer or film 52 and the associated manufacturing techniques in accordance with the invention are now described. From the start at Block 90 of the flow chart 88, magnetizable particles 93 are mixed in a hardenable or solidifiable fluid 91a (FIG. 7) at Block 92. The magnetizable particles 93 may be iron or ferrous particles in one example, although those skilled in the art will appreciate that there are other material particles that may be similarly aligned by application of a magnetic field.

Figure 7:
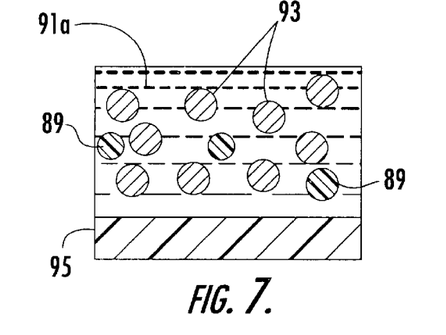
FIG. 7 is a greatly enlarged schematic cross-sectional view of a fluid layer including spherical magnetizable particles before alignment and curing in accordance with the method of the present invention.

The viscosity of the fluid 91a may also be readily controlled by the addition or incorporation of dielectric particles 89 of predetermined sizes and/or at a predetermined concentration as will be readily appreciated by those skilled in the art. The dielectric particles 89 may also reduce undesired lateral coupling of the magnetizable particles 93 as will also be readily appreciated by those skilled in the art.

Figure 8:
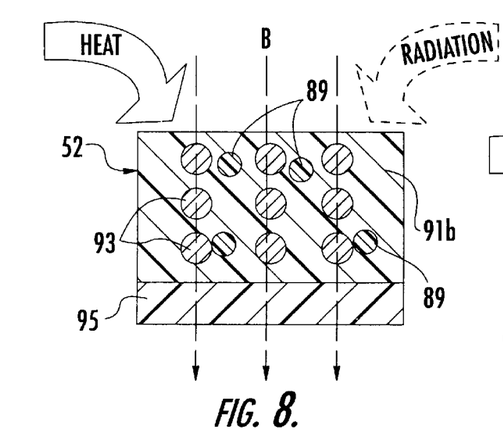
FIG. 8 is a schematic cross-sectional view of the fluid layer of FIG. 7 after alignment of the magnetizable particles and curing of the fluid material in accordance with the method of the present invention.

For the embodiment shown in FIGS. 7 and 8, the magnetizable particles 93 have a generally spherical shape and diameters in the range of about 1 to 3 $\mu$m. The hardenable fluid 91a may be a curable liquid, such as a polyimide, for example, or a thermoplastic or thermosetting material as will be appreciated by those skilled in the art. The solidifiable or hardenable fluid 91a may also be a mixture of such materials as will also be readily appreciated by those skilled in the art.

Figure 4:
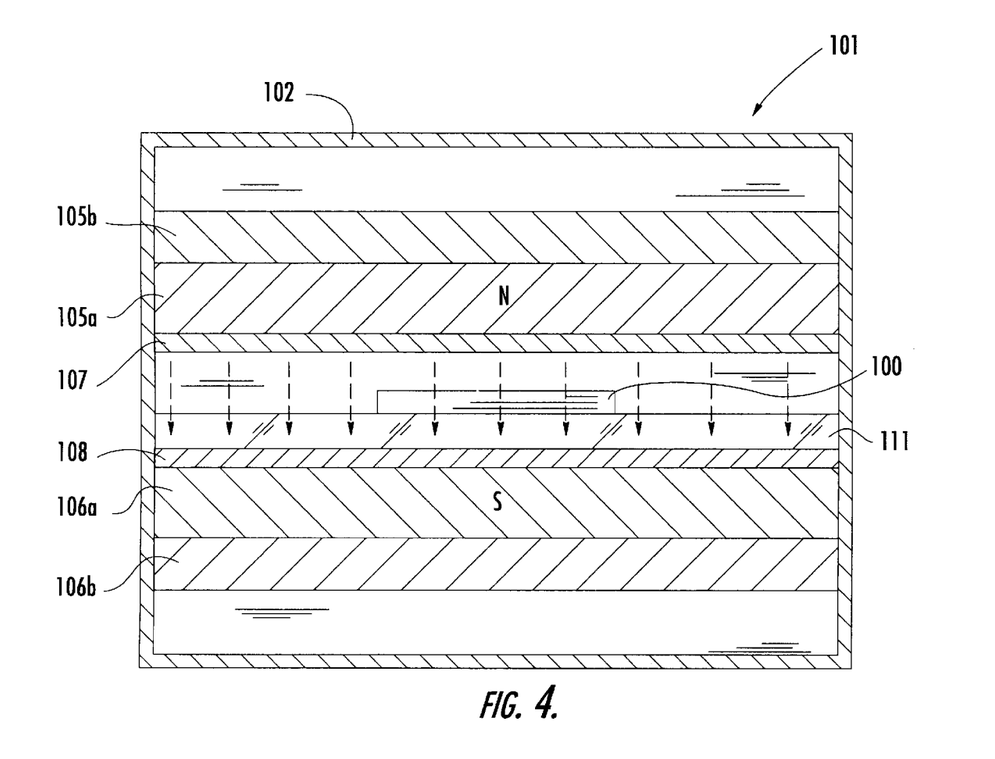
FIG. 4 is a schematic cross-sectional view of an apparatus for carrying out the method for making the anisotropic dielectric layer in accordance with the present invention.
Figure 5:
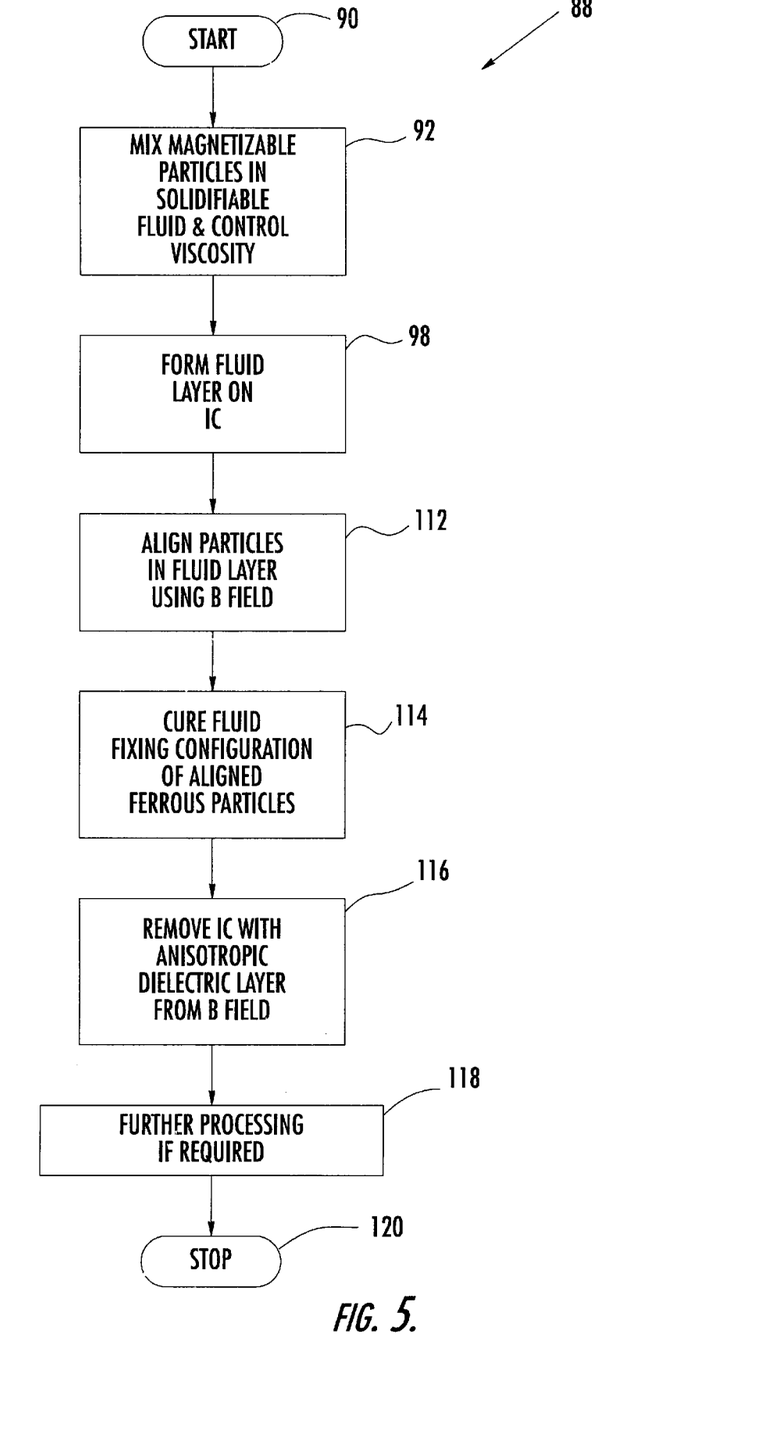
FIG. 5 is a flow chart illustrating the method for making the anisotropic dielectric layer in accordance with the present invention.

At Block 98 the solidifiable fluid 91a including the magnetizable particles 93 is applied to the upper surface portion 95 of an integrated circuit die, such as the fingerprint sensor 30. More particularly, as shown in FIG. 4, an entire wafer 100 including a plurality of fingerprint sensing dies may be positioned in the chamber 102 of the apparatus 101. The fluid 91a may be applied by conventional spin coating techniques, for example, although those of skill in the art will recognize other deposition techniques as well.

The apparatus 101 illustratively includes a pair of upper permanent magnets 105a, 105b and a pair of lower permanent magnets 106a, 106b to provide a sufficiently large magnetic field. The pairs of magnets are positioned in vertically spaced relation. The magnets desirably generate a substantially uniform magnetic field between them in the range of about 400 to 1000 Gauss. Of course, the strength of the magnetic field can be varied based upon spacings, materials, etc. as will be readily appreciated by those skilled in the art. In addition, as will also be appreciated by those skilled in the art, electromagnets could also be used in addition to or in lieu of the permanent magnets. The magnets 105a, 105b, 106a and 106b desirably extend past the edges of the wafer 100 so that the magnetic field will be uniform even at the edges.

Respective aluminum plates 107, 108 are positioned adjacent the upper magnet 105a and the lower magnet 106a as shown in the illustrated embodiment. A glass plate 111 is positioned on the lower aluminum plate 108. The wafer 100 is positioned on top of the glass plate 111 in about the center of the chamber to thereby be exposed to a relatively uniform magnetic field as indicated by the dashed arrows.

The magnetic field aligns the magnetizable particles 93 along the magnetic field lines (Block 112) and as schematically illustrated in FIG. 7 (nonaligned) and FIG. 8 (after aligning). At Block 114 the fluid is cured to its final hardened state defining the solid matrix of material 91b as shown in FIG. 8. As will be readily appreciated by those skilled in the art, the curing or hardening may be affected by applying heat or radiation (FIG. 8), such as ultraviolet or laser radiation, to any of a number of curable materials as would also be readily appreciated by those skilled in the art. Other suitable materials may be cured by application of an electric field, for example, as will also be appreciated by those skilled in the art. The solidifiable fluid 91a may also be a self-curing material, or one that cures upon evaporation of a solvent, although a heat-cured or radiation-cured material may be preferred for greater controllability.

The curable fluid 91a may have sufficient viscosity so that once the magnetizable particles 93 are aligned they remain in a stable position until the fluid cures and without constant application of the magnetic field. Of course, the viscosity can be controlled by the incorporation of dielectric particles 89 as explained above. In other words, for certain materials, the magnetic field may be applied, and the wafer 100 may then be removed from the chamber 102 for curing, and without effecting the alignment of the particles. Alternately, it may be desirable to cure the fluid 91a while the magnetic field is still applied as will be readily appreciated by those skilled in the art. Accordingly, the apparatus 101 may be fitted with a heater or radiation emitting device to effect curing in the same process while the wafer 100 is positioned in the chamber 102 and is exposed to the magnetic field.

Once the fluid is cured to yield the solidified matrix 91b (FIG. 8), the anisotropic dielectric layer is thus defined having a so-called z-axis anisotrophy wherein the electrical impedance in a direction perpendicular to the layer is less than an impedance parallel to the layer. By perpendicular to the layer is meant normal to the major surface of the layer as will be understood by those skilled in the art. Accordingly, for an embodiment where the curing occurs in the chamber 102, at Block 116 the wafer 100 may be removed and subjected to further processing (Block 118), such as dicing into individual integrated circuits before stopping at Block 120.

Figure 6:
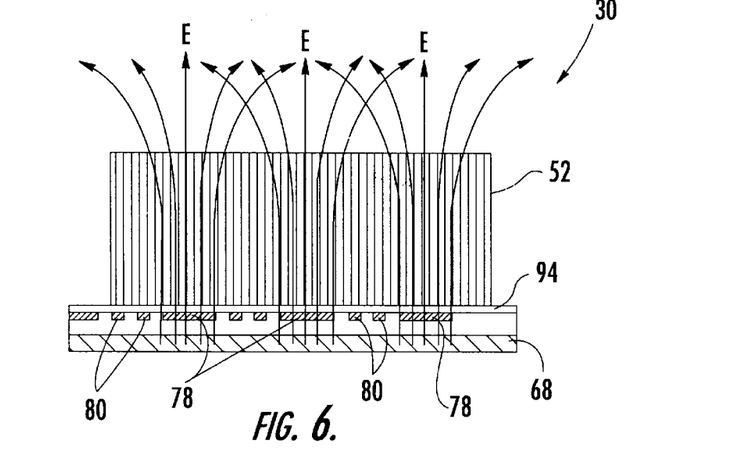
FIG. 6 is a schematic cross-sectional view of the fingerprint sensor including the anisotropic dielectric layer in accordance with the present invention and illustrating the focusing effect of the anisotropic dielectric layer.

Referring briefly in particular to FIG. 6, a portion of the integrated circuit fingerprint sensor 30 is described with the outer layer being provided by the z-axis anisotropic dielectric layer 52. In the illustrated embodiment, there is also a thin passivation layer 94 on the electrodes 78, 80 and underlying the anisotropic dielectric layer 52. The thin passivation layer 94 may comprise a thin oxide, nitride, carbide, or diamond layer as will be appreciated by those skilled in the art.

As schematically illustrated by the electric field lines E, the electric field is more constrained or focused upon passing through the z-axis anisotropic dielectric layer 52. In other words, if the layer were not an anisotropic layer, the electric field lines would diverge, and focus would be reduced. Accordingly, the resolution of the sensor 30 would suffer as will be appreciated by those skilled in the art. Typically there would be a trade-off between field focus and mechanical protection. Unfortunately, a thin film which is desirable for focusing, may permit the underlying circuit to be more easily subject to physical or chemical damage. The anisotropic dielectric layer 52 in accordance with the present invention overcomes this limitation as it provides both a relatively thick protective layer, and enhances electric focusing therethrough.

The anisotropic dielectric layer 52 of the present invention, for example, may have a thickness in range of about 0.0004 to 0.004 inches. Other thickness are also possible. Of course, the anisotropic dielectric layer 52 is also preferably chemically resistant and mechanically strong to withstand contact with fingers, and to permit periodic cleanings with solvents when used for the fingerprint sensor 30. The anisotropic dielectric layer 52 may preferably define an outermost protective surface for the fingerprint sensor 30. The anisotropic dielectric layer 52 may also be desirably softer than the passivation layer 94 to thereby absorb more mechanical activity.

Figure 9:
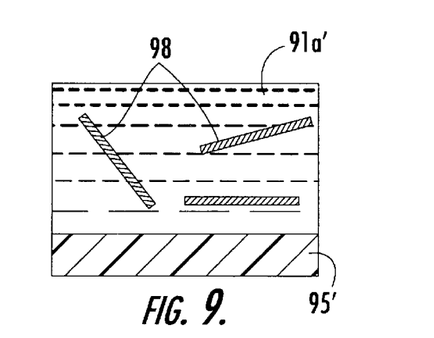
FIG. 9 is a greatly enlarged schematic cross-sectional view of a fluid layer including elongate magnetizable particles before alignment and curing in accordance with a second embodiment of the method of the present invention.
Figure 10:
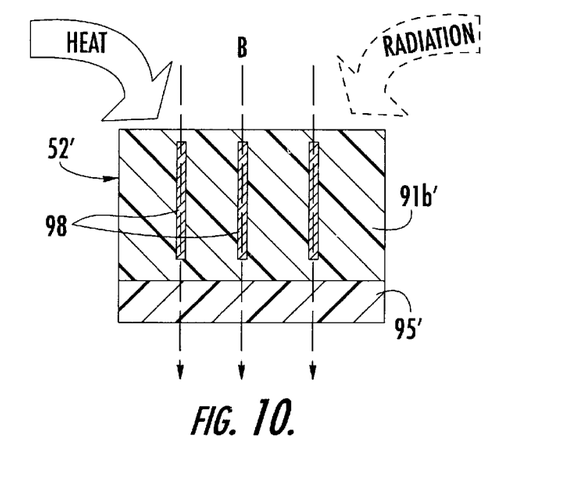
FIG. 10 is a schematic cross-sectional view of the fluid layer of FIG. 9 after alignment of the elongate magnetizable particles and curing of the fluid material in accordance with the second embodiment of the method of the present invention.

Turning now to FIGS. 9 and 10, an alternate embodiment of magnetizable particles 98 is illustrated in the unaligned and uncured state (FIG. 9), and the aligned and cured state (FIG. 10). In this embodiment, the magnetizable particles 98 are elongate in shape, and align with the magnetic field so that their longitudinal axes align with the magnetic field lines as would be readily understood by those skilled in the art. In this illustrated embodiment, the dielectric particles are not shown, but could be readily used as will be appreciated by those skilled in the art. The other elements shown in FIGS. 9 and 10 are indicated with prime notation and are similar to those in FIGS. 7 and 8 described above.

Figure 11:
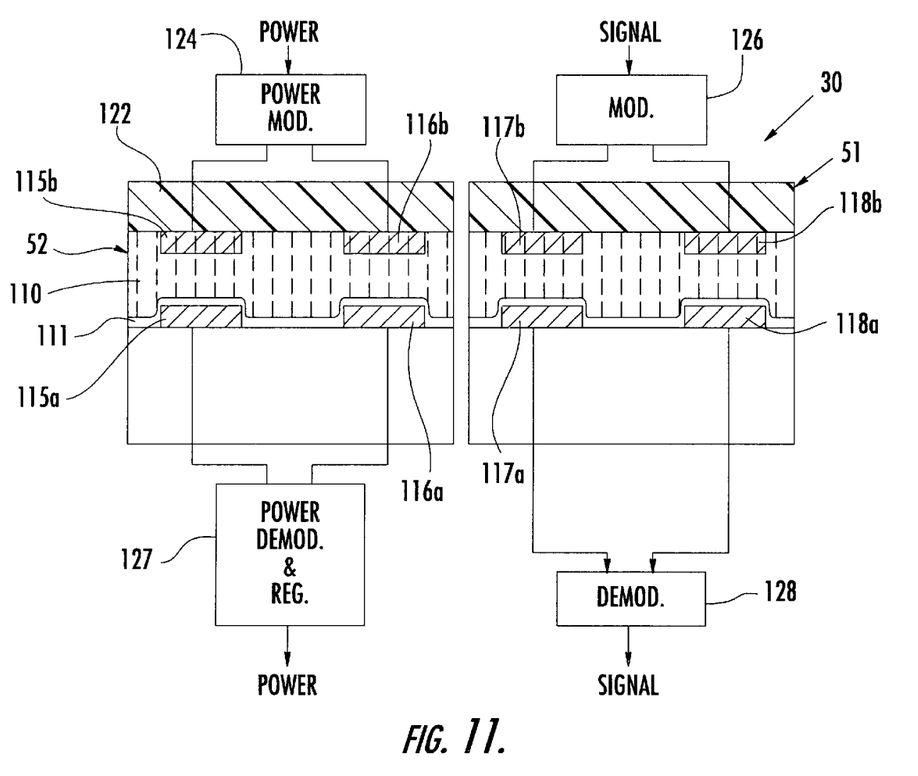
FIG. 11 is a schematic view, partially in section, of another application of the anisotropic dielectric layer in accordance with the present invention for facilitating capacitive coupling through the layer.

Referring now to FIG. 11, another application of the anisotropic dielectric covering 52' is explained. The anisotropic dielectric layer 52 may be used to completely cover and protect the entire upper surface of the integrated circuit die of the fingerprint sensor 30 and still permit connection and communication with the external devices and circuits.

The third metal layer 71 (FIG. 2) may further include a plurality of capacitive coupling pads 116a–118a for permitting capacitive coupling of the integrated circuit die. Accordingly, the anisotropic dielectric covering 52 is preferably continuous over the capacitive coupling pads 116a–118a and the array of electric field sensing electrodes 78 of the pixels 30a (FIG. 1). In sharp contrast to this feature of the present invention, it is conventional to create openings through an outer coating to electrically connect to the bond pads. Unfortunately, these openings would provide pathways for water and/or other contaminants to come in contact with and damage the die.

A portion of the package 51 includes a printed circuit board 122 which carries corresponding pads 115b–118b. A power modulation circuit 124 is coupled to pads 115b–116b, while a signal modulation circuit 126 is illustratively coupled to pads 117b–118b. As would be readily understood by those skilled in the art, both power and signals may be readily coupled between the printed circuit board 122 and the integrated circuit die further using the illustrated power demodulation/regulator circuit 127, and the signal demodulation circuit 128. The z-axis anisotropic dielectric layer 52 also advantageously reduces cross-talk between adjacent capacitive coupling pads. This embodiment of the fingerprint sensor 30 presents no penetrations through the dielectric layer 52 for moisture to enter and damage the integrated circuit die. In addition, another level of insulation is provided between the integrated circuit and the external environment.

In one example, a magnetic strength of about 700 Gauss on the top of the glass plates was applied to a mixture comprising 30 wt % iron powder roll milled with polyimide PI 2808. Non-magnetic and non-magnetizable substrates were used. After spin coating on the substrate, the films were placed in the apparatus 101 as described above. An infrared heat lamp gently dried the film while the specimen was exposed to the magnetic field. The heating was relatively slow, about 5 to 10 minutes with the infrared heat source at about 1 foot separation, so the surface was dried evenly. The specimen was allowed to cool before being removed from the magnetic field. The specimen was then cured as follows: heated at a rate of 3° C./min to 300° C., held at 300° C. for 60 minutes, and then allowed to cool naturally.

In other example, 15 wt % iron and 15 wt % aluminum oxide was used in a PI 2808 fluid. The paste coating was allowed to stand for a relatively long time period of about 5 hours to harden, so that the particles were not disturbed when being removed from between the magnets. The heat lamp was positioned at a minimum distance of about 20 cm and not applied for longer than 5 minutes. The results were that the unaligned mix seemed to be uniform and homogenous, at least as good as the roll prepared paste. The magnetically aligned coatings showed alignment of iron particles in columns. This alignment occurred both in mixes with or without dielectric particles, such as $Al_2O_3$, being added. It is believed that the dielectric particles are effective to control viscosity, while also reducing the lateral coupling of the magnetizable particles. The electrical anisotropy of the films was found to about 35:1.

Figure 12:
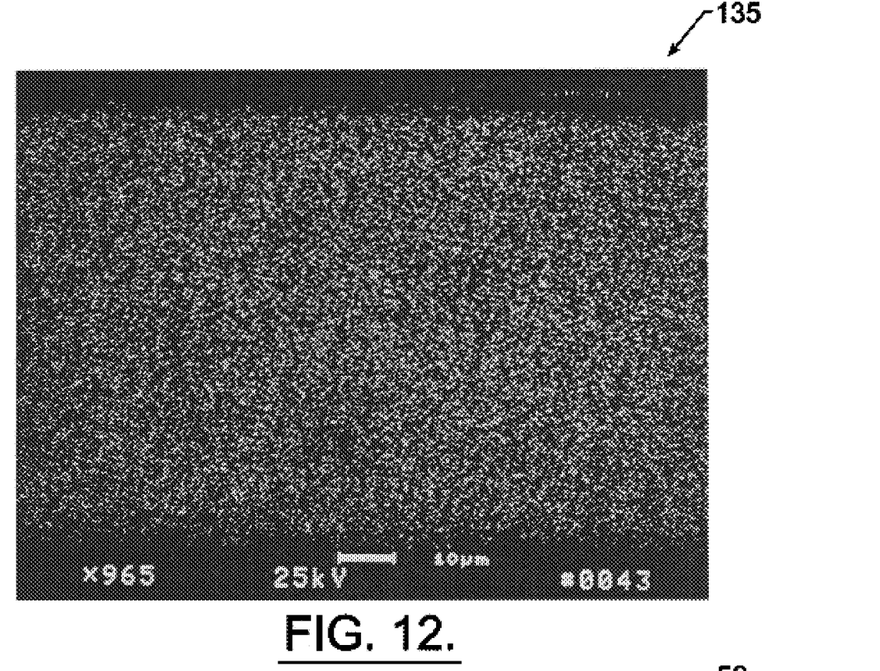
FIG. 12 is a photomicrograph of a cured fluid with the magnetizable particles in an unaligned condition.
Figure 13:
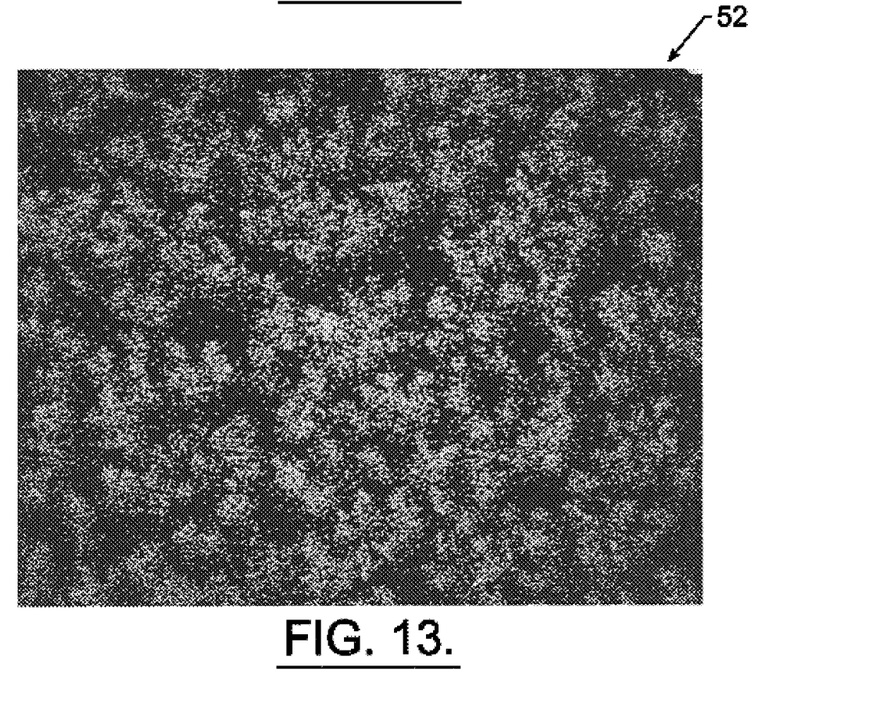
FIG. 13 is a photomicrograph of the cured fluid with the magnetizable particles aligned at an angle to the viewing direction and at the same magnification as FIG. 12.
Figure 14:
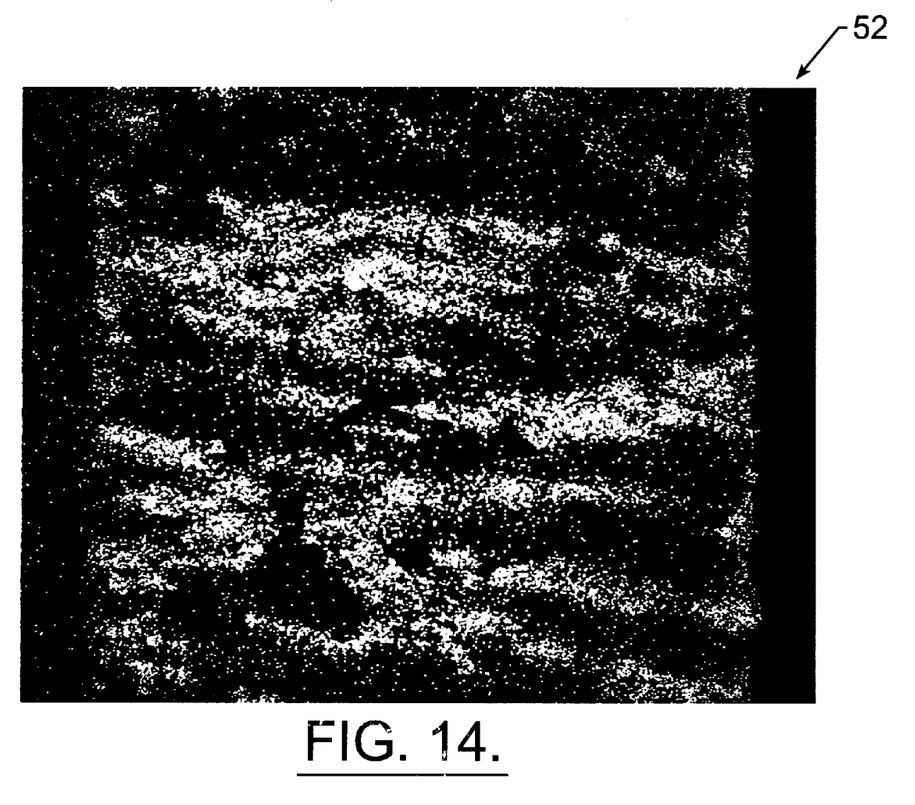
FIG. 14 is a photomicrograph of the cured fluid and aligned magnetizable particles as shown in FIG. 13, but at a higher magnification.

A photomicrograph of a dielectric layer 135 including magnetizable particles in an random configuration, that is, in a cured matrix without being magnetically aligned, is shown in FIG. 12. The surface of the film 135 illustrated particles that appear random in arrangement. In contrast, the photomicrographs of FIGS. 13 and 14 show the anisotropic dielectric layer 52 wherein the magnetizable particles have been magnetically aligned. The surface of the anisotropic dielectric layer 52 presents regular repeating grouped particles illustrating that the magnetic alignment and curing have been effective.

Other aspects, advantages, and features relating to sensing of fingerprints are disclosed in copending U.S. patent application Ser. No. 08/592,469 entitled "Electric Field Fingerprint Sensor and Related Methods", and U.S. patent application Ser. No. 08/671,430 entitled "Integrated Circuit Device Having an Opening Exposing the Integrated Circuit Die and Related Methods", both assigned to the assignee of the present invention, and the entire disclosures of which are incorporated herein by reference. Of course, the anisotropic dielectric layer and associated method of making same may be used in many other semiconductor, imaging, and/or image sensing devices. In addition, the direction of alignment of the magnetizable particles 93, 98 may be readily controlled to define other than z-axis anisotropy as will be readily appreciated by those skilled in the art.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A method for making an anisotropic dielectric layer on a surface of an integrated circuit comprising the steps of:
    forming a fluid layer onto the surface of the integrated circuit, the fluid layer comprising a plurality of magnetizable particles in a fluid;
    aligning the magnetizable particles of the fluid layer in a configuration by applying a magnetic field thereto; and
    fixing the aligned magnetizable particles in the configuration within a dielectric matrix by solidifying the fluid to thereby make the anisotropic dielectric layer on the surface of the integrated circuit so that the anisotropic dielectric layer is substantially electrically non-conductive between opposing faces thereof.

2. A method according to claim 1 wherein the step of aligning comprises aligning the magnetizable particles in a configuration by applying a magnetic field thereto so that an impedance in a direction perpendicular to the anisotropic dielectric layer is less than an impedance in a direction parallel to the anisotropic dielectric layer.

3. A method according to claim 1 further comprising the step of mixing the magnetizable particles in a curable polymer fluid; and wherein the step of fixing the aligned magnetizable particles comprises curing the curable polymer fluid.

4. A method according to claim 1 further comprising the step of controlling a viscosity of the fluid by incorporating dielectric particles in the fluid.

5. The method according to claim 1 wherein forming the fluid layer comprises spin coating the fluid layer onto the surface of the integrated circuit.

6. A method for making an anisotropic dielectric layer on an integrated circuit fingerprint sensor comprising:
    spin coating a surface of the integrated circuit fingerprint sensor with a fluid layer comprising a plurality of magnetizable particles in a fluid;
    aligning the magnetizable particles of the fluid layer in a configuration by applying a magnetic field thereto; and
    fixing the aligned magnetizable particles in the configuration within a dielectric matrix by solidifying the fluid to thereby make the anisotropic dielectric layer on the surface of the intergrated circuit fingerprint sensor so that the anisotropic dielectric layer is substantially electrically non-conductive between opposing faces thereof.

7. A method according to claim 6 wherein aligning comprises aligning the magnetizable particles in a configuration by applying a magnetic field thereto so that an impedance in a direction perpendicular to the anisotropic dielectric layer is less than an impedance in a direction parallel to the anisotropic dielectric layer.

8. A method according to claim 6 further comprising mixing the magnetizable particles in a curable polymer fluid; and wherein fixing the aligned magnetizable particles comprises curing the curable polymer fluid.

9. A method according to claim 6 further comprising controlling a viscosity of the fluid by incorporating dielectric particles in the fluid.

* * * * *